US012060600B2

(12) United States Patent
Ishidou et al.

(10) Patent No.: US 12,060,600 B2
(45) Date of Patent: Aug. 13, 2024

(54) TOMATO PATHOGENIC FUNGUS DETECTING APPARATUS AND DETECTING METHOD USING SAME

(71) Applicant: Panasonic Intellectual Property Management Co., Ltd., Osaka (JP)

(72) Inventors: Tarou Ishidou, Kyoto (JP); Yosifumi Kariatumari, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 18/146,209

(22) Filed: Dec. 23, 2022

(65) Prior Publication Data

US 2023/0136396 A1 May 4, 2023

Related U.S. Application Data

(63) Continuation of application No. 17/069,905, filed on Oct. 14, 2020, now abandoned, which is a continuation of application No. PCT/JP2019/015049, filed on Apr. 5, 2019.

(30) Foreign Application Priority Data

May 23, 2018 (JP) ................................ 2018-098830

(51) Int. Cl.
*C12Q 1/04* (2006.01)
*C12M 1/34* (2006.01)

(52) U.S. Cl.
CPC ............ *C12Q 1/045* (2013.01); *C12M 41/46* (2013.01)

(58) Field of Classification Search
None
See application file for complete search history.

(56) References Cited

U.S. PATENT DOCUMENTS

| | | | | |
|---|---|---|---|---|
| 5,126,257 A | 6/1992 | Gabay et al. | | |
| 9,695,459 B2 * | 7/2017 | Uriu | ......................... | C12N 1/14 |
| 10,767,209 B2 * | 9/2020 | Weaver | .................... | C12Q 1/04 |
| 2017/0037445 A1 | 2/2017 | Uriu | | |
| 2019/0048388 A1 | 2/2019 | Yamaguchi et al. | | |

FOREIGN PATENT DOCUMENTS

| | | |
|---|---|---|
| JP | 2005-287337 | 10/2005 |
| JP | 6167309 B | 7/2017 |
| WO | 2018/011835 | 1/2018 |

OTHER PUBLICATIONS

Shirane et al. Ann Phytopathol Soc Japan, 1987, 53, pp. 191-197.*
International Search Report of PCT application No. PCT/JP2019/015049 dated Jul. 9, 2019.
Paul F. Morris et al., "Chemotropic and Contact Responses of Phytophthora sojae Hyphae to Soybean Isoflavonoids and Artificial Substrates", Plant Physiol. (1998)117: 1171-1178.
Noboru Shirane et al., "Mineral Salt Medium for the Growth of Botrytis cinerea in vitro", Ann. Phytopath. Soc. Japan 53: 191-197 (1987).
Izumi Sasaki et al., "β-Glucosidase from Botrytis cinerea: Its Relation to the Pathogenicity of This Fungus", Bioscience, Biotechnology, and Biochemistry, 1994, vol. 58, No. 4, pp. 616-620.
Akira Kaji et al., "Studies on the Pectic Enzymes Part XXII. Pectic Enzymes Produced by Botrytis cinerea and Relation between Enzymatic Actions and Maceration of Plant Tissues", Journal of the Agricultural Chemical Society of Japan, vol. 40, No. 4, pp. 209-212, 1966.
Mari Hakkinen et al., "The effects of extracellular pH and of the transcriptional regulator PACI on the transcriptome of Trichoderma reesei", Microbial Cell Factories, 2015, vol. 14:63, pp. 1-15.
Justus et al. "In vitro cell migration and invasion assays". Journal of Visualized Experiments. 2014, (88), e51064, pp. 1-8; published Jun. 1, 2014.
Non-Final Office Action dated Mar. 23, 2022 issued in U.S. Appl. No. 17/069,905.
Final Office Action dated Sep. 27, 2022 issued in U.S. Appl. No. 17/069,905.
English Translation of Chinese Search Report dated Nov. 1, 2023 for the related Chinese Patent Application No. 201980018208.7.

* cited by examiner

*Primary Examiner* — Vera Afremova
(74) *Attorney, Agent, or Firm* — Rimon P.C.

(57) ABSTRACT

The present disclosure provides a simple and secure apparatus and a simple and secure method for selectively detecting a tomato pathogenic fungus. The tomato pathogenic fungus detecting apparatus according to the present disclosure is characterized by including an artificial cell wall, a test sample solution inlet provided above the artificial cell wall, and a culture solution storage part provided under the artificial cell wall, wherein a test sample solution contains a 50 mM to 70 mM buffer solution of a citrate salt in the test sample solution inlet, and the test sample solution has a pH of 5 to 5.5.

4 Claims, 9 Drawing Sheets

FIG. 6

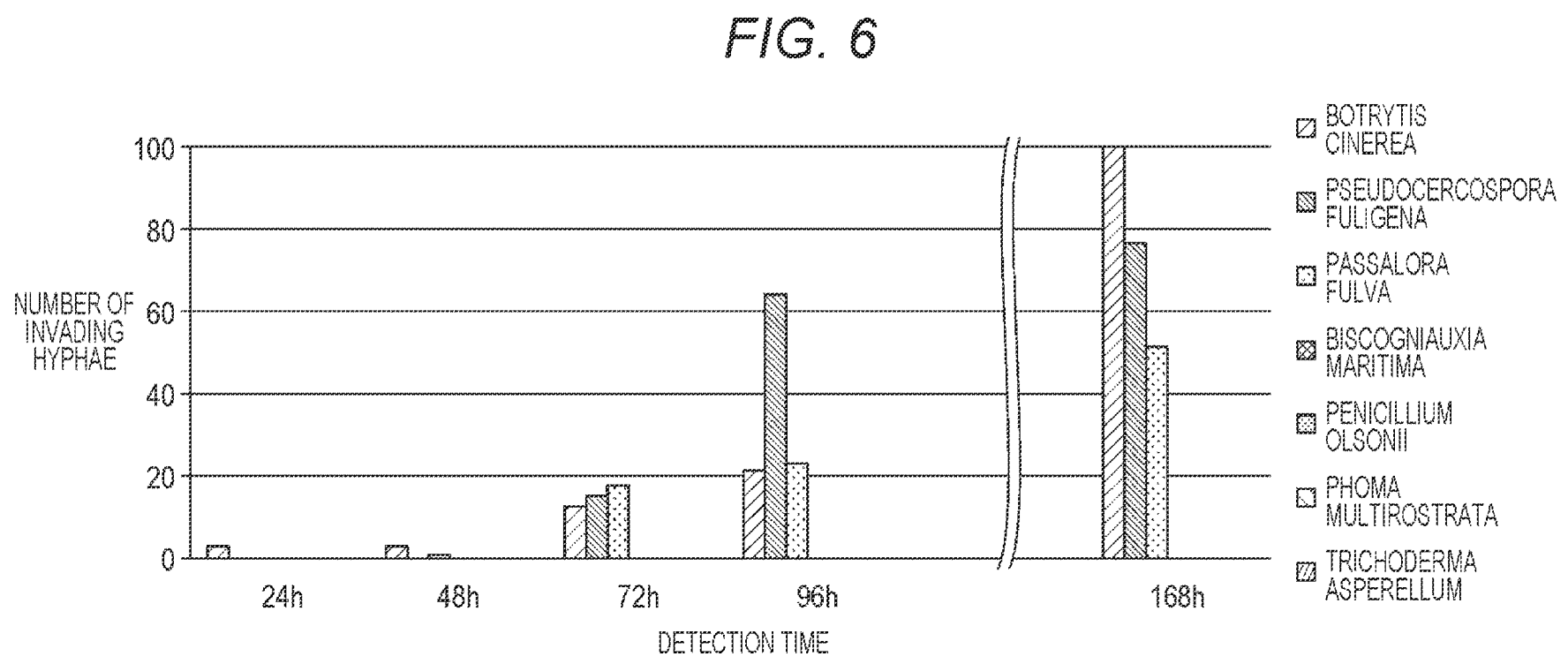

NUMBER OF INVADING HYPHAE 100
80
60
40
20
0

24h
48h
72h
96h
168h

DETECTION TIME

BOTRYTIS CINEREA
PSEUDOCERCOSPORA FULIGENA
PASSALORA FULVA
BISCOGNIAUXIA MARITIMA
PENICILLIUM OLSONII
PHOMA MULTIROSTRATA
TRICHODERMA ASPERELLUM

NUMBER OF INVADING HYPHAE
50
40
30
20
10
0
FUNGUS
BOTRYTIS CINEREA
PSEUDOCERCOSPORA FULIGENA
PASSALORA FULVA
BISCOGNIAUXIA MARITIMA
PENICILLIUM OLSONII
PHOMA MULTIROSTRATA
TRICHODERMA ASPERELLUM

TOMATO PATHOGENIC FUNGUS DETECTING APPARATUS AND DETECTING METHOD USING SAME

CROSS-REFERENCE TO RELATED APPLICATIONS

This application is a Divisional of U.S. patent application Ser. No. 17/069,905, filed on Oct. 14, 2020, which is a Continuation of International Patent Application No. PCT/JP2019/015049, filed on Apr. 5, 2019, which claims the benefit of foreign priority of Japanese Patent Application No. 2018-098830, filed on May 23, 2018, the contents all of which are incorporated herein by reference.

TECHNICAL FIELD

The present invention relates to a tomato pathogenic fungus detecting apparatus and a selective detecting method using the tomato pathogenic fungus detecting apparatus.

BACKGROUND ART

Phytopathogenic fungi have, as properties involving invasiveness into plants, features of forming an appressorium on a surface of a plant for attachment, and then searching for a pore, such as a stoma tissue, through which a hypha is extended into a plant body or secreting a plant cell wall degrading enzyme (a cellulase or a pectinase) from a hypha.

Making use of these features, for example, PTL 1 discloses a method for measuring an amount of a fungus using a microporous membrane support. NPL 1 discloses facts that a pseudohypha of *Phytophthora sojae* as one type of phytopathogenic oomycete grows downward as if attempting to go deep, rather than growing horizontally and that the pseudohypha penetrates a PET (polyethylene terephthalate) membrane having a pore of 3 μm.

Focusing on this property, the inventors of the present invention have already proposed a method for determining a phytopathogenic oomycete (PTL 2).

CITATION LIST

Patent Literatures

PTL 1: Japanese Patent Application Publication No. 2005-287337

PTL 2: Japanese Patent No. 6,167,309

PTL 3: WO 2018/011835 A

Non-Patent Literatures

NPL 1: Paul F. Morris. et. al. "Chemotropic and Contact Responses of *Phytophthora sojae* Hyphae to Soybean Isoflavonoids and Artificial Substrates", Plant Physiol. (1998) 117: 1171-1178

NPL 2: Noboru Shirane et al., "Mineal Salt Medium for the Growth of *Botrytis cinerea* in vitro", Ann. Phytopath. Soc. Japan 53: 191-197 (1987)

SUMMARY OF THE INVENTION

Technical Problem

A target plant in the present invention, tomatoes are highly prone to disease caused by fungi, and pathogenic fungi that cause the disease are said to be dominated by three types of fungi, a tomato gray mold fungus (*Botrytis cinerea*, a tomato sooty mold fungus (*Pseudocercospora fuligena*), and a tomato leaf mold fungus (*Passalora fulva*). With regard to these pathogenic fungi, the gray mold fungus (*Botrytis cinerea*) is plurivorous and is infectious also to other plants, but the sooty mold fungus (*Pseudocercospora fuligena*) and the leaf mold fungus (*Passalora fulva*) present examples of infection only to tomatoes and are pathogenic fungi having high plant specificity. With regard to these pathogenic fungi that are said to have specificity to tomatoes, the inventors of the present invention have considered that it is necessary to detect the tomato pathogenic fungi in a stage where it is unclear what type of fungus is present on actual tomato leaves, that is, in a stage before pathogenesis, and have studied on this subject.

On the other hand, a pathogenic fungus selection technique using an artificial cell wall that is a basic selective fungus detection technique described in PTL 2 and used by the inventors of the present invention probably detects not only the tomato pathogenic fungi but also any phytopathogenic fungi. That is, if a fungus pathogenic to another plant is attached to a tomato leaf, the pathogenic fungus selection technique may possibly detect the fungus as a tomato pathogenic fungus. Tomato cultivation is mostly performed not by seeds but by seedlings, and a possibility cannot be ruled out of attaching a phytopathogenic fungus other than the tomato pathogenic fungi to a tomato seedling in a nursery garden, due to mixed cultivation with other plants and sharing of tools among a plurality of plants in a same facility. Similarly to the nursery garden described above, there is a possibility of attaching a fungus pathogenic to a plant other than tomatoes to a tomato seedling also in an actual cultivation site and a cultivation facility such as a vinyl greenhouse. If such attachment is left untreated, the phytopathogenic fungus other than the tomato pathogenic fungi possibly leads to presentation of a false positive in the pathogenic fungus selection technique using an artificial cell wall, to sometimes cause severe inconvenience in cultivation, such as useless chemical application or renewal of seedlings.

As a result of a research and investigation on this possibility of generating a false positive, the inventors of the present invention have actually encountered fungi that are other than the tomato pathogenic fungi and that lead to presentation of a false positive in a studying detecting method using an artificial cell wall. The fungi are four types of fungi, a *Biscogniauxia* genus fungus, a *Penicillium* genus fungus, a *Phoma* genus fungus, and a *Trichoderma* genus fungus, and a study on a method that does not detect these fungi has been required.

The present invention has been made in view of such actual circumstances, and an object of the present invention is to provide an apparatus and a method for selectively detecting a tomato pathogenic fungus.

Solution to Problem

As a result of an earnest study, the inventors of the present invention and others have found that a detecting apparatus configured as below can solve the above problem and further conducted the study based on the finding to complete the present invention.

That is, a tomato pathogenic fungus detecting apparatus related to one aspect of the present invention is characterized by including an artificial cell wall, a test sample solution inlet provided above the artificial cell wall, and a culture solution storage part provided under the artificial cell wall, wherein a test sample solution contains a 50 mM to 70 mM buffer solution of a citrate salt in the test sample solution inlet, and the test sample solution has a pH of 5 to 5.5.

Advantageous Effects of Invention

The present invention is capable of providing an apparatus and a method that are capable of selectively detecting a tomato pathogenic fungus simply and safely. The present invention enables presence of a tomato pathogenic fungus to be detected in a stage before pathogenesis caused by the fungus and enables presentation of a false positive attributed to a phytopathogenic fungus other than tomato pathogenic fungi to be avoided in the detection, so that the present invention is very useful for industrial use.

BRIEF DESCRIPTION OF DRAWINGS

FIG. 6 shows a graph illustrating results of Example 1.

DESCRIPTION OF EMBODIMENT

Hereinafter, an embodiment according to the present invention is specifically described. The present invention, however, is not limited to this embodiment.

Figure 1:
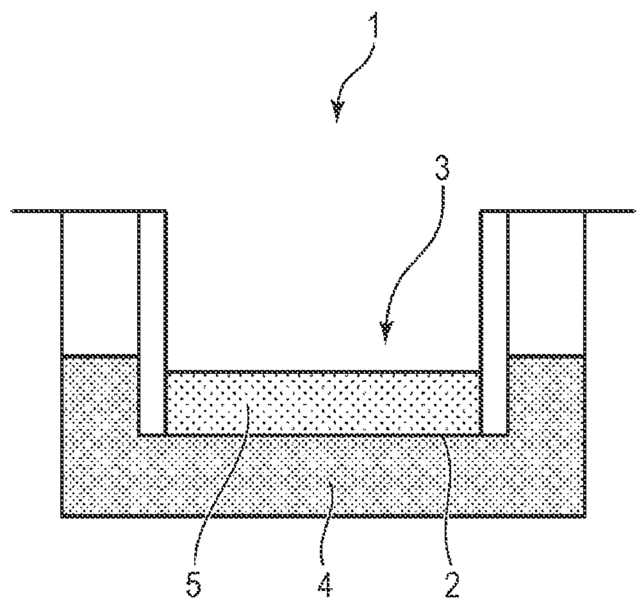
FIG. 1 shows a schematic sectional view illustrating one example of a detecting apparatus of the present embodiment.

Tomato pathogenic fungus detecting apparatus 1 according to the present embodiment is characterized by including, as illustrated in FIG. 1, artificial cell wall 2, test sample solution inlet 3 provided above artificial cell wall 2, and culture solution storage part 4 provided under artificial cell wall 2. Test sample solution 5 contains a 50 mM to 70 mM buffer solution of a citrate salt in test sample solution inlet 3. Test sample solution 5 has a pH of 5 to 5.5.

Test sample solution inlet 3 is a vessel into which test sample solution 5 is charged, and the vessel desirably includes a flange on an upper end of the vessel. A bottom surface of test sample solution inlet 3 is formed of artificial cell wall 2.

Figure 2:
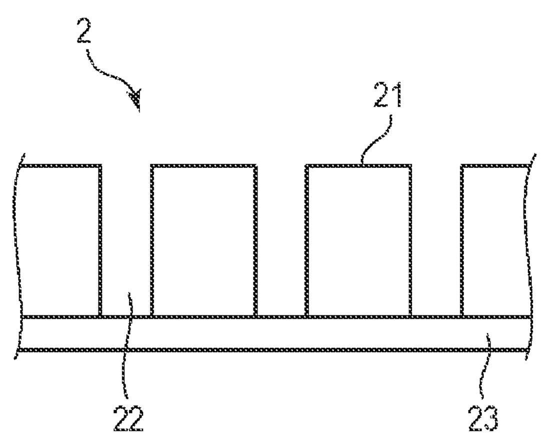
FIG. 2 shows a schematic sectional view illustrating one example of an artificial cell wall included in the detecting apparatus of the present embodiment.

Artificial cell wall 2 preferably includes, as illustrated in FIG. 2, at least substrate 21 having through hole 22, and cellulose membrane 23 provided on one surface of substrate 21. Use of such an artificial cell wall further facilitates selective detection of a targeted tomato pathogenic fungus.

Through hole 22 penetrates from a front-end surface to a back-end surface of substrate 21, and the through hole preferably has a hole diameter of 2 μm to 7 μm (sectional area of 4.5 $\mu m^2$ to 38.5 $\mu m^2$). The through hole having a hole diameter in the above range enables a target pathogenic fungus to be selectively detected more securely.

Further, in order to selectively detect a target pathogenic fungus more securely, a thickness of cellulose membrane 23 is also preferably adjusted. Specifically, cellulose membrane 23 preferably has a thickness of 0.5 μm to 2 μm.

It is considered that in artificial cell wall 2 of the present embodiment, adjusting the hole diameter of through hole 22 in substrate 21 and the membrane thickness of cellulose membrane 23 in the above range does not allow many of tomato non-pathogenic fungi to penetrate cellulose membrane 23, so that a part of the tomato non-pathogenic fungi can be excluded in this stage. On the other hand, a tomato pathogenic fungus targeted in the present embodiment selectively appears on the back surface of the substrate.

A thickness of substrate 21 is not particularly limited, but is preferably about 5 μm to 150 μm as one example.

As illustrated in FIG. 1, test sample solution 5 is supplied into test sample solution inlet 3. Thus, if test sample solution 5 contains a tomato pathogenic fungus, the tomato pathogenic fungus comes to be present on the front-end surface of substrate 21.

In the present embodiment, test sample solution 5 is mainly a solution (fungus collection solution) containing a fungus attached to a tomato leaf, and is not particularly limited as long as the test sample solution is a liquid probably containing a target pathogenic fungus. The test sample solution is, for example, a liquid having been used to wash a tomato leaf or a liquid in which a tomato leaf has been immersed.

In the present embodiment, it is important that test sample solution 5 has a pH of 5 to 5.5 and test sample solution 5 contains a 50 mM to 70 mM buffer solution of a citrate salt. These configurations enable obstructive fungi (tomato non-pathogenic fungi) that lead to a false positive in pathogenic fungus detection to be excluded and thus enable a target tomato pathogenic fungus to be selectively detected.

Test sample solution 5 having a pH of less than 5 or more than 5.5 may possibly make it impossible to completely exclude the tomato non-pathogenic fungi that obstruct the tomato pathogenic fungus detection. The test sample solution that contains the buffer solution having a concentration of the citrate salt of less than 50 mM may possibly make it impossible to completely exclude the tomato non-pathogenic fungi that obstruct the tomato pathogenic fungus detection. On the other hand, the test sample solution that contains the buffer solution having a concentration of the citrate salt of more than 70 mM may possibly also exclude a part of targeted tomato pathogenic fungi.

The citrate salt is not particularly limited, but is preferably a monovalent citrate salt, and is preferably sodium citrate, potassium citrate, or the like more specifically.

Further, test sample solution 5 normally preferably has an EC (electric conductivity) of about 7 mS/cm to 15 mS/cm.

The tomato pathogenic fungus targeted by the detecting apparatus of the present embodiment is preferably at least one selected from a tomato gray mold fungus (*Botrytis cinerea*), a tomato sooty mold fungus (*Pseudocercospora fuligena*), or a tomato leaf mold fungus (*Passalora fulva*).

The detecting apparatus of the present embodiment preferably does not detect fungi that are sometimes present on tomato leaves but are tomato non-pathogenic fungi, e.g., a *Biscogniauxia* genus fungus, a *Penicillium* genus fungus, a

*Phoma* genus fungus, and a *Trichoderma* genus fungus. More specifically, the tomato non-pathogenic fungi are *Biscogniauxia maritima, Penicillium olsonii, Phoma multirostrata*, and *Trichoderma asperellum*.

In the present specification, the term "tomato pathogenic" means being pathogenic to tomatoes. The term "tomato non-pathogenic" means being non-pathogenic to tomatoes. A fungus that is pathogenic but is not pathogenic to tomatoes is "tomato non-phytopathogenic". In other words, a fungus that does not adversely affect tomatoes is "tomato non-pathogenic". The prefix "non-" included in the term "tomato non-pathogenic" does not modify the "tomato", but modifies the "pathogenic".

In the detecting apparatus of the present embodiment, a culture solution is put in culture solution storage part 4 provided under artificial cell wall 2. The culture solution is not particularly limited as long as the culture solution is capable of culturing a fungus, and a general culture medium or culture solution is usable. For example, general culture media for culturing a fungus, i.e., a potato dextrose culture medium, Sabouraud dextrose culture medium, and the like are usable. In order to accelerate the culture of a fungus, a culture solution may be added not only to culture solution storage part 4 but also to test sample solution 5.

Figure 3:
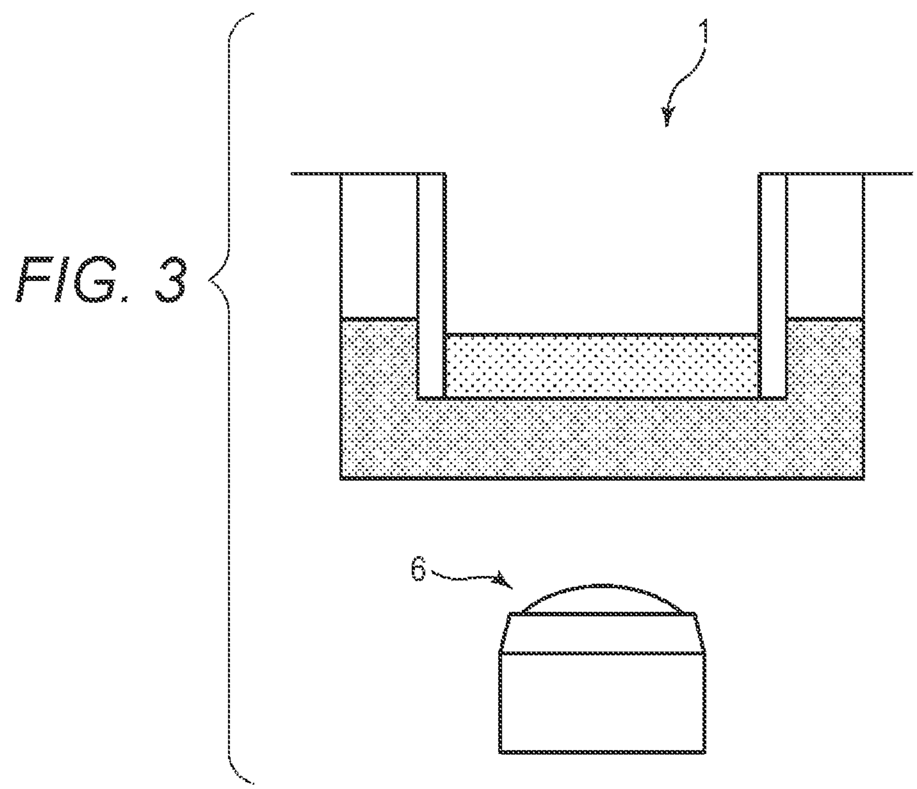
FIG. 3 shows a schematic sectional view illustrating one example of the detecting apparatus of the present embodiment.

The detecting apparatus of the present embodiment detects presence or absence of a tomato pathogenic fungus in a sample by observing, after a lapse of a certain culture period, whether or not the tomato pathogenic fungus has appeared on the back surface of cellulose membrane 23 of artificial cell wall 2. An observation means is not particularly limited, and optical observation can be conducted with microscope 6 by disposing microscope 6 under artificial cell wall 2 as illustrated in FIG. 3.

The culture period of a fungus is not particularly limited and is preferably not less than 72 hours. A culture temperature is preferably set at about 20° C. to 28° C.

The present invention further encompasses a tomato pathogenic fungus detecting method including selectively detecting a tomato pathogenic fungus using the detecting apparatus described above.

The tomato pathogenic fungus detecting method of the present embodiment is not particularly limited in terms of steps other than using the detecting apparatus described above, and includes the steps of, for example: charging a test sample solution into test sample solution inlet 3 of the detecting apparatus; leaving the test sample solution to stand still in the detecting apparatus (culturing); observing a back surface of artificial cell wall 2 (cellulose membrane 23) in the detecting apparatus after the leaving; and determining that the test sample solution contains a tomato pathogenic fungus when the fungus is observed on the back surface of cellulose membrane 23.

The present specification discloses various forms of techniques as described above, from among which main techniques are summarized as follows.

A tomato pathogenic fungus detecting apparatus according to one aspect of the present invention is characterized by including an artificial cell wall, a test sample solution inlet provided above the artificial cell wall, and a culture solution storage part provided under the artificial cell wall, wherein a test sample solution contains a 50 mM to 70 mM buffer solution of a citrate salt in the test sample solution inlet, and the test sample solution has a pH of 5 to 5.5.

These configurations enable provision of an apparatus and a method that are capable of selectively detecting a tomato pathogenic fungus simply and safely.

In the detecting apparatus, it is preferable that the artificial cell wall includes at least a substrate that has a through hole with a hole diameter of 2 μm to 7 μm and has a thickness of 5 μm to 150 μm, and a cellulose membrane that is provided on one surface of the substrate and has a thickness of 0.5 μm to 2 μm. These configurations are considered to enable the effects described above to be more securely obtained.

In the detecting apparatus, the citrate salt is preferably at least one selected from sodium citrate or potassium citrate. This setting is considered to enable the effects described above to be more securely obtained.

In the detecting apparatus, a tomato pathogenic fungus to be a detection target is preferably at least one selected from a tomato gray mold fungus (*Botrytis cinerea*), a tomato sooty mold fungus (*Pseudocercospora fuligena*), or a tomato leaf mold fungus (*Passalora fulva*). This setting is considered to enable the effects described above to be more exhibited.

The detecting apparatus preferably does not detect fungi that are sometimes present on tomato leaves but are tomato non-pathogenic fungi, namely a *Biscogniauxia* genus fungus, a *Penicillium* genus fungus, a *Phoma* genus fungus, and a *Trichoderma* genus fungus. This setting is considered to enable the effects described above to be more exhibited.

The tomato non-pathogenic fungi are more preferably *Biscogniauxia maritima, Penicillium olsonii, Phoma multirostrata*, and *Trichoderma asperellum*.

A tomato pathogenic fungus detecting method according to another aspect of the present invention is characterized by selectively detecting a tomato pathogenic fungus using the detecting apparatus.

Hereinafter, the present invention is described further specifically by way of an example. A scope of the present invention, however, is not limited to this example.

EXAMPLE

[Preparation of Fungi]

(Culture of *Botrytis cinerea*)

*Botrytis cinerea*, which is one of tomato pathogenic fungi and a pathogenic fungus of tomato gray mold disease was inoculated into a potato dextrose agar culture medium (Difco™ Potato Dextrose Agar). Next, the culture medium was left to stand still at a temperature of 25 degrees Celsius for one week. *Botrytis cinerea* was given by associate professor Shimizu belonging to Faculty of Applied Biological Sciences, Gifu University. Thereafter, the *Botrytis cinerea*-cultured potato dextrose agar culture medium in which hyphae sufficiently grew was left under irradiation with black light for not less than four days and left in a room-temperature environment for not less than two weeks to promote spore formation. Several ml of sterile pure water was dropped to the treated *Botrytis cinerea*-cultured potato dextrose agar culture medium, and surfaces of the hyphae were rubbed with a platinum loop, an ink brush, or the like to give a crushed hypha and spore mixed suspension.

(Culture of *Pseudocercospora fuligena*)

*Pseudocercospora fuligena*, which is one of tomato pathogenic fungi and a pathogenic fungus of tomato sooty mold disease was inoculated into a potato dextrose agar culture medium. Next, the culture medium was left to stand still at a temperature of 28 degrees Celsius for one week. *Pseudocercospora fuligena* was gotten from The Genetic Resources Center, NARO (the National Agriculture and Food Research Organization) (MAFF No. 306728). Thereafter, hyphae of *Pseudocercospora fuligena* were transplanted from the potato dextrose agar culture medium to a burdock powder agar culture medium, and further left to stand still at a temperature of 28 degrees Celsius for one to two weeks. After sufficiently growing again, the hyphae was subjected to mechanical stress such as rubbing surfaces of the hyphae with a platinum loop, an ink brush, or the like, thereafter left under irradiation with black light for not less than four days, and then left in a room-temperature environment for not less than two weeks to promote spore formation again. Several ml of sterile pure water was dropped to the treated *Pseudocercospora fuligena*-cultured burdock powder agar culture medium, and surfaces of the hyphae were rubbed with a platinum loop, an ink brush, or the like to give a crushed hypha and spore mixed suspension.

(Culture of *Passalora fulva*)

*Passalora fulva*, which is one of tomato pathogenic fungi and a pathogenic fungus of tomato leaf mold disease was inoculated into a potato dextrose agar culture medium. Next, the culture medium was left to stand still at a temperature of 23 degrees Celsius for one to two weeks. *Passalora fulva* was gotten from The Genetic Resources Center, NARO (the National Agriculture and Food Research Organization) (MAFF No. 726744). Thereafter, several ml of sterile pure water was dropped to the *Passalora fulva*-cultured potato dextrose agar culture medium in which hyphae sufficiently grew, and surfaces of the hyphae were rubbed with a platinum loop, an ink brush, or the like to give a crushed hypha and spore mixed suspension.

(Culture of *Biscogniauxia maritima, Penicillium Olsonii, Phoma Multirostrata*, and *Trichoderma Asperellum*)

*Biscogniauxia maritima, Penicillium olsonii, Phoma multirostrata*, and *Trichoderma asperellum* that were not tomato pathogenic fungi but were present on tomato leaves were collected from the tomato leaves, separated, and then inoculated into a potato dextrose agar culture medium. Separation sources, tomatoes were collected from a plurality of locations. A separation method was as follows. Collected several tomato leaves were charged into a clear resin vessel or a resin bag together with a fungus collection solution that consists of saline containing 0.1% of surfactant Tween 80 (SIGMA-ALDRICH), stirred for one minute to transfer fungi attached to the leaves to the fungus collection solution. The fungus collection solution was diluted and applied to a potato dextrose agar culture medium containing 100 mg/L of streptomycin sulfate (Wako Pure Chemical Industries, Ltd.) by a plate agar smear method. Then, fungi that emerged in culture at 25 degrees Celsius for several days were separated from a fungus colony. Identification of the fungi was commissioned to Japan Food Research Laboratories (general incorporated foundation), Tama Laboratory. After the isolation, *Biscogniauxia maritima, Penicillium olsonii, Phoma multirostrata*, and *Trichoderma asperellum* that were inoculated into potato dextrose agar culture media were left to stand still at a temperature of 25 degrees Celsius for one week. Thereafter, several ml of sterile pure water was dropped to the potato dextrose agar culture media for culturing these four types of fungi in which hyphae sufficiently grew or spores were sufficiently formed, and surfaces of the hyphae were rubbed with a platinum loop, an ink brush, or the like to give a crushed hypha and spore mixed suspension.

[Preparation of Artificial Cell Wall]

The artificial cell wall in the detecting apparatus was prepared as follows.

First, cellulose (SIGMA-ALDRICH, trade name: Avicel PH-101) was dissolved in an ionic liquid to prepare a cellulose solution having a concentration of 1%. The ionic liquid was 1-Butyl-3-methyl imidazolium chloride (manufactured by SIGMA-ALDRICH). The cellulose solution was heated to 60 degrees Celsius and next applied to a back surface of a vessel (Millipore, trade name: Millicell PISP 12R 48) including a polyethylene terephthalate film as a bottom surface by spin coating for 30 seconds at a rotation rate of 2000 rpm. The polyethylene terephthalate film functioned as substrate 21 of the artificial cell wall in FIG. 2 and randomly had a plurality of through holes with a diameter of 3 μm. Thus, a cellulose membrane having a thickness of 0.5 micrometers was formed on a back-end surface of the polyethylene terephthalate film.

The vessel including the cellulose membrane formed on the back surface of the polyethylene terephthalate film as the bottom surface was left to stand still in ethanol for 12 hours at room temperature. Thus, 1-Butyl-3-methyl imidazolium chloride was replaced with ethanol and removed, and then the vessel was dried in a vacuum desiccator at the end. Thus, the artificial cell wall was obtained that was tested in the present example and comparative examples.

[Preparation of Tomato Pathogenic Fungus Detecting Apparatus]

The vessel that was formed into the artificial cell wall and included the cellulose membrane on the back surface of the polyethylene terephthalate film (substrate) as the bottom surface was put on a culture medium vessel (culture solution storage part) to form a tomato pathogenic fungus detecting apparatus. As the culture medium vessel, a 24-well flat bottom culture plate (Corning Incorporated, trade name: 24 Well Cell Cluture Cluster Flat Bottom) was used, and a space between the culture medium vessel and the artificial cell wall-forming vessel was filled with 600 μL of a liquid culture medium (culture solution) so that the back surface of the artificial cell wall-forming vessel was in contact with the liquid culture medium. As the liquid culture medium, a diluted potato dextrose liquid culture medium (Difco™ Potato Dextrose Broth 2.4 g/L aqueous solution) was used.

Example 1

The crushed hypha and spore mixed suspensions respectively containing 200 pieces of hyphae and spores of *Botrytis cinerea, Pseudocercospora fuligena, Passalora fulva, Biscogniauxia maritima, Penicillium olsonii, Phoma multirostrata*, and *Trichoderma asperellum* were separately added into the artificial cell wall-forming vessel, and a sodium citrate buffer solution was added to the vessel in the example so that a total volume of each of the resultant crushed hypha and spore mixed suspensions and the sodium citrate buffer solution became 200 μL. Thus, test sample solutions were obtained. The sodium citrate buffer solution was prepared and added so that a concentration of the sodium citrate buffer solution contained in the test sample solution became 60 mM when the sodium citrate buffer solution was mixed with the crushed hypha and spore mixed suspension to give a volume of 200 μL. The sodium citrate buffer solution added into the artificial cell wall-forming vessel had a pH of 5.5 and an EC of 13 mS/cm.

Figure 4:
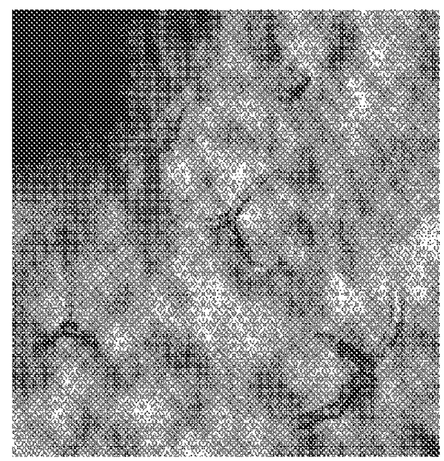
FIG. 4 shows a micrograph of a back surface of an artificial cell wall illustrating a state where a tomato gray mold fungus (*Botrytis cinerea*) has penetrated the artificial cell wall in Example 1.

Then, the test sample solutions respectively containing the seven types of fungi were disposed in the prepared detecting apparatus, which was left to stand still at a temperature of 25 degrees Celsius and subjected to observation at intervals of 24 hours. A number of hyphae that penetrated the artificial cell wall and observed on the back surface of the artificial cell wall was counted every 24 hours by visual inspection via an optical microscope. FIG. 4 shows one example (tomato gray mold fungus (*Botrytis cinerea*)) of observation photographs captured with the optical microscope.

Comparative Example 1

A test was performed similarly to in Example 1 except that sterile purified water was used in place of the sodium citrate buffer solution.

[Consideration]

Figure 5:
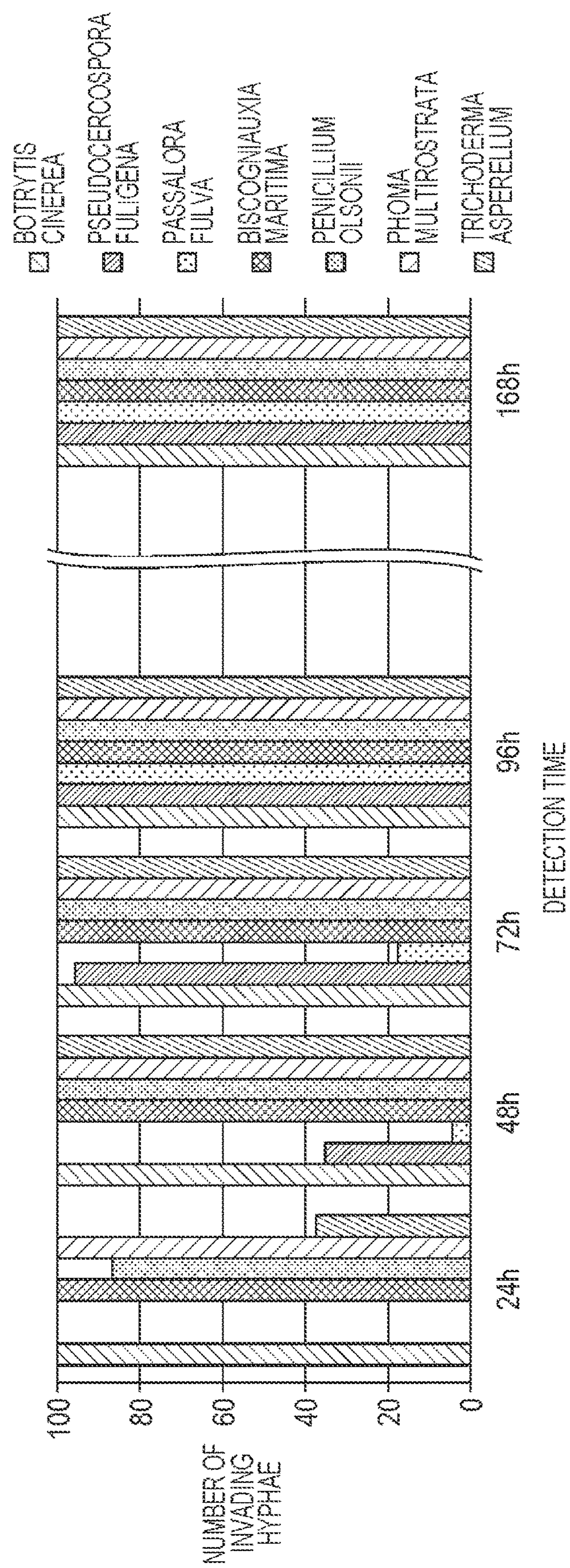
FIG. 5 shows a graph illustrating results of Comparative Example 1.

FIG. 5 shows results of Comparative Example 1 and FIG. 6 shows results of Example 1.

FIG. 5 shows that hyphae having penetrated the artificial cell wall were observed earlier in the four types of tomato non-pathogenic fungi that were sometimes present on tomato leaves but were to be excluded from the detection, namely *Biscogniauxia maritima, Penicillium olsonii, Phoma multirostrata*, and *Trichoderma asperellum*, than in the tomato pathogenic fungi to be detected, namely *Pseudocercospora fuligena* and *Passalora fulva*. Thus, the tomato pathogenic fungi could not be selectively detected in the present comparative example.

In contrast, FIG. 6 representing the results of the example shows that hyphae having penetrated the artificial cell wall were, at 72 h, observed earlier in the tomato pathogenic fungi, *Botrytis cinerea, Pseudocercospora fuligena*, and *Passalora fulva* than in the four types of tomato non-pathogenic fungi that were sometimes present on tomato leaves but were to be excluded from the detection, namely *Biscogniauxia maritima, Penicillium olsonii, Phoma multirostrata*, and *Trichoderma asperellum*. Thus, it was confirmed that the tomato pathogenic fungi could be selectively detected in Example 1.

Comparative Example 2

Figure 7:
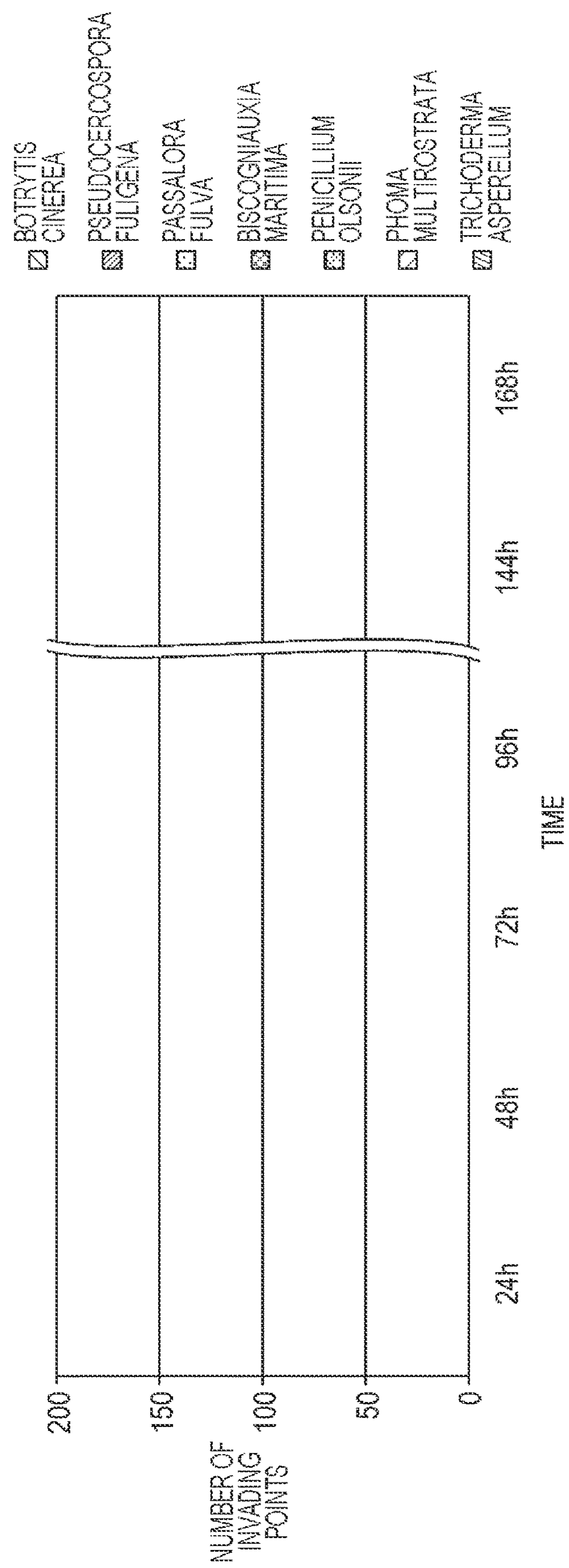
FIG. 7 shows a graph illustrating results of Comparative Example 2.

A test was performed similarly to in Example 1 except that a sodium citrate buffer solution having the same concentration (60 mM) as in the test sample solution was charged also into the culture medium of the detecting apparatus and the culture solution was prepared to also have a pH of 5.5. FIG. 7 shows results.

As is clear from FIG. 7, any of the fungi neither penetrated the artificial cell wall nor grew in Comparative Example 2.

Comparative Example 3

Figure 8:
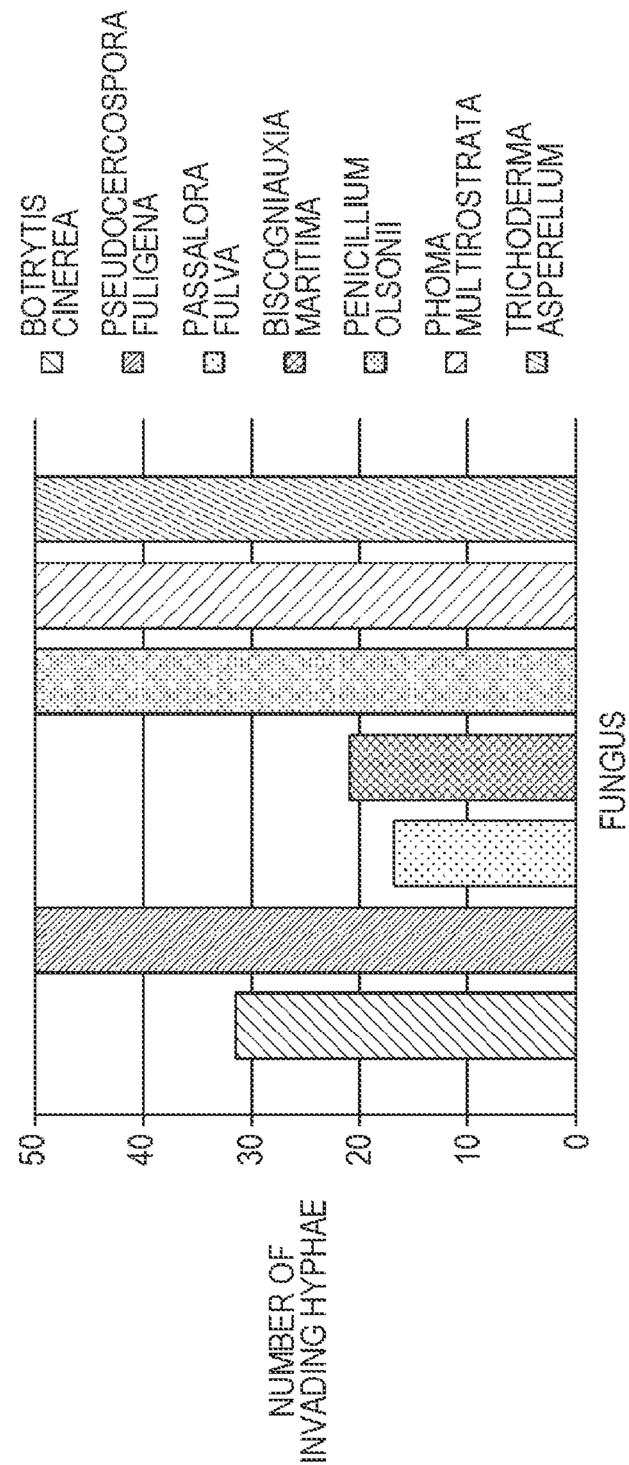
FIG. 8 shows a graph illustrating results of Comparative Example 3.

A test was performed similarly to in Example 1 except that the pH of the test sample solution was changed to 4.5. FIG. 8 shows results of the number of invading hyphae after 72 hours of the culture in Comparative Example 3.

As is clear from FIG. 8, a part of the obstructive fungi (tomato non-pathogenic fungi) penetrated the artificial cell wall, and the obstructive fungi could not be completely excluded in Comparative Example 3.

Comparative Example 4

Figure 9:
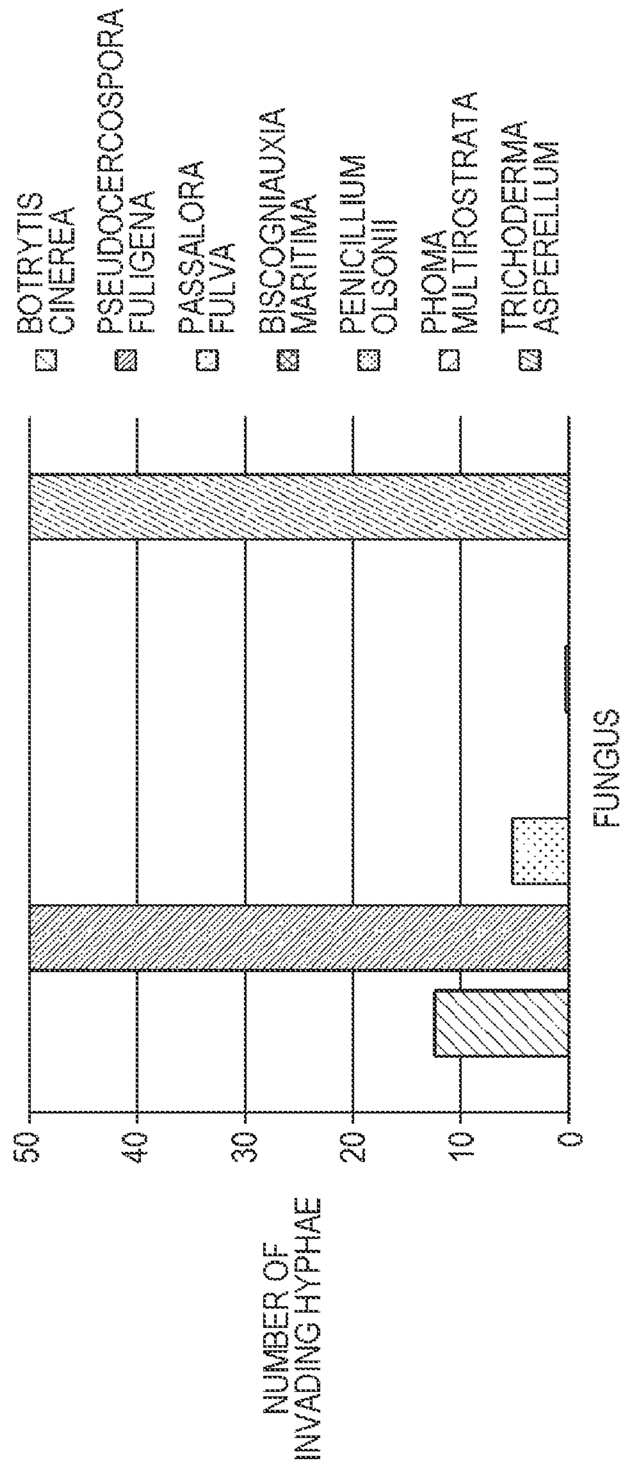
FIG. 9 shows a graph illustrating results of Comparative Example 4.

A test was performed similarly to in Example 1 except that the pH of the test sample solution was changed to 6. FIG. 9 shows results of the number of invading hyphae after 72 hours of the culture in Comparative Example 4.

As is clear from FIG. 9, a part of the obstructive fungi (tomato non-pathogenic fungi) penetrated the artificial cell wall, and the obstructive fungi could not be completely excluded also in Comparative Example 4.

The results of Comparative Examples 3 and 4 above indicated that the pH of the test sample solution is one of important factors for selectively detecting a tomato pathogenic fungus.

Comparative Example 5

Figure 10:
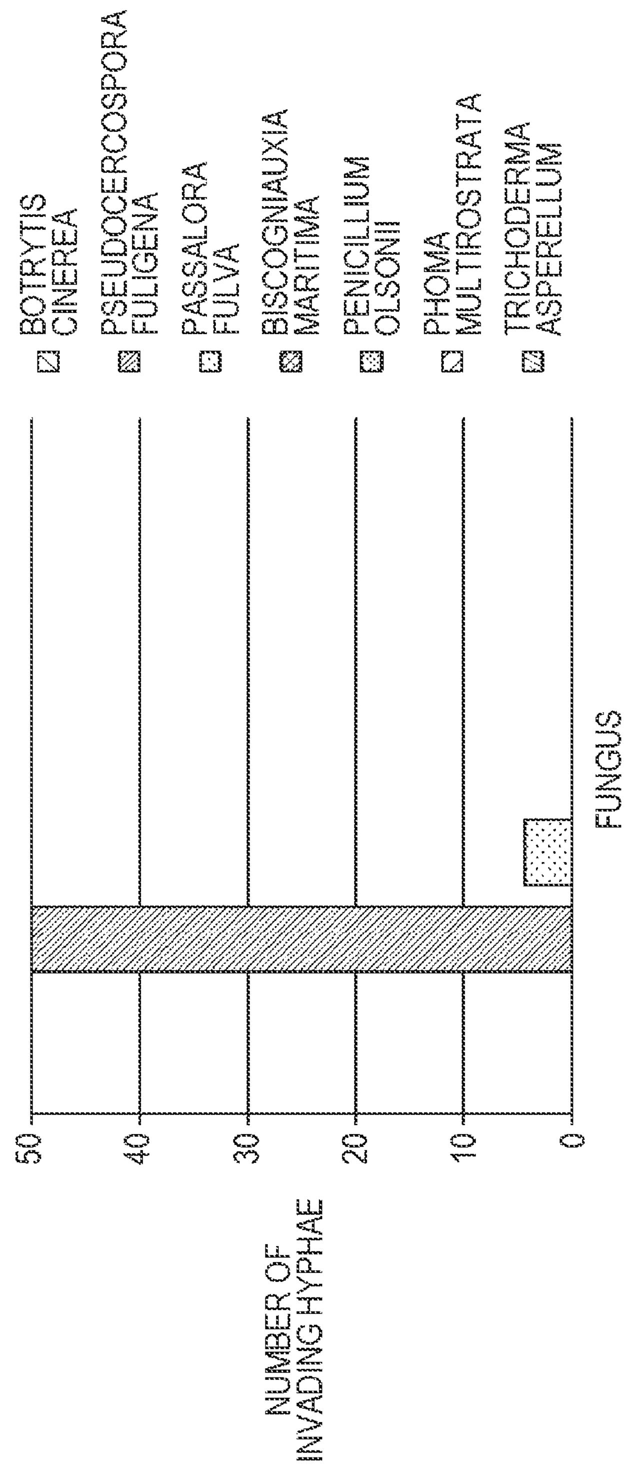
FIG. 10 shows a graph illustrating results of Comparative Example 5.

A test was performed similarly to in Example 1 except that the pH of the test sample solution was set at 5 and the concentration of the sodium citrate buffer solution contained in the test sample solution was set at 100 mM. FIG. 10 shows results of the number of invading hyphae after 72 hours of the culture in Comparative Example 5.

The results in FIG. 10 made it understandable that Comparative Example 4 not only excluded the obstructive fungi (tomato non-pathogenic fungi) but also a part of the target tomato pathogenic fungi.

Comparative Example 6

Figure 11:
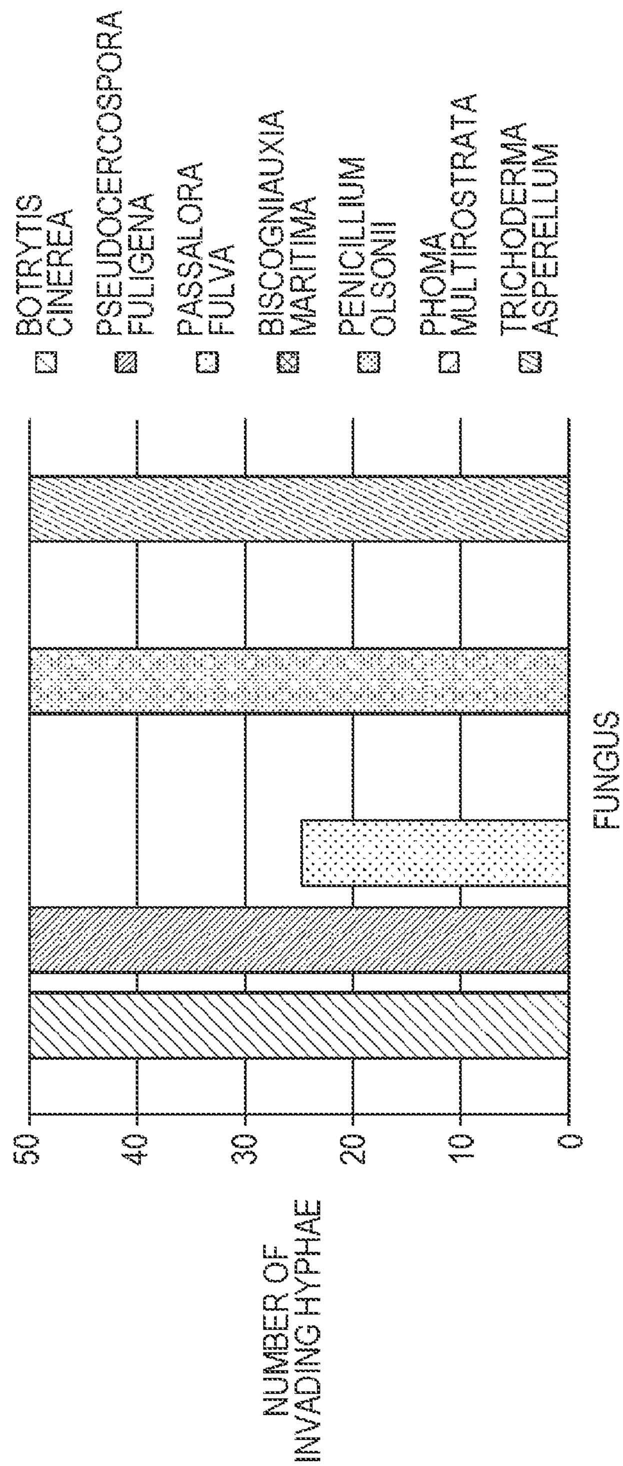
FIG. 11 shows a graph illustrating results of Comparative Example 6.

A test was performed similarly to in Example 1 except that the pH of the test sample solution was set at 5 and the concentration of the sodium citrate buffer solution contained in the test sample solution was set at 40 mM. FIG. 11 shows results of the number of invading hyphae after 72 hours of the culture in Comparative Example 6.

As is clear from FIG. 11, a part of the obstructive fungi (tomato non-pathogenic fungi) penetrated the artificial cell wall, and the obstructive fungi could not be completely excluded in Comparative Example 6.

The results of Comparative Examples 5 and 6 above indicated that the concentration of the sodium citrate buffer solution contained in the test sample solution is one of important factors for selectively detecting a tomato pathogenic fungus.

INDUSTRIAL APPLICABILITY

A tomato pathogenic fungus detecting apparatus of the present disclosure is capable of selectively detecting a target tomato pathogenic fungus while excluding a tomato non-pathogenic fungus leading to a false positive. Therefore, the detecting apparatus of the present disclosure can be suitably utilized for removing a tomato pathogenic fungus that adversely affects tomatoes or for other purposes in technical fields such as agriculture involving tomatoes.

REFERENCE SIGNS LIST

1 detecting apparatus
2 artificial cell wall
3 test sample solution inlet
4 culture solution storage part
5 test sample solution
6 microscope
21 substrate
22 through hole
23 cellulose membrane

The invention claimed is:

1. A detection method of a tomato pathogenic fungus using a detecting apparatus comprising an artificial cell wall, a test sample solution inlet provided above the artificial cell wall, and a culture solution storage part provided under the artificial cell wall, the method comprising:

charging a test sample solution into the test sample solution inlet, wherein the test sample solution contains a 50 mM to 70 mM buffer solution of a citrate salt, and the test sample solution has a pH of 5 to 5.5, leaving the test sample solution to stand still in the detecting apparatus, observing a lower surface of the artificial cell wall, and determining that the test sample solution contains a tomato pathogenic fungus when a fungus is observed on the lower surface of the artificial cell wall, wherein the test sample solution contains at least one selected from the group consisting of tomato gray mold fungus *Botrytis cinerea*, tomato sooty mold fungus *Pseudocercospora fuligena*, and a tomato leaf mold fungus *Passalora fulva*, and wherein even if any of a *Biscogniauxia* genus fungus, a *Penicillium* genus fungus, a *Phoma* genus fungus, and a *Trichoderma* genus fungus, these four of which are tomato non-pathogenic fungi, is included in the test sample solutions, none of the *Biscogniauxia* genus fungus, the *Penicillium* genus fungus, the *Phoma* genus fungus, and the *Trichoderma* genus fungus is detected.

2. The detection method of the tomato pathogenic fungus according to claim 1, wherein the artificial cell wall includes a substrate that has a through hole with a hole diameter of 2 μm to 7 μm and has a thickness of 5 μm to 150 μm, and a cellulose membrane that is provided on one surface of the substrate and has a thickness of 0.5 μm to 2 μm.

3. The detection method of the tomato pathogenic fungus according to claim 1, wherein the citrate salt is at least one selected from the group consisting of sodium citrate and potassium citrate.

4. The detection method of the tomato pathogenic fungus according to claim 1, wherein, among the tomato non-pathogenic fungi, the *Biscogniauxia* genus fungus is *Biscogniauxia maritima,* the *Penicillium* genus fungus is *Penicillium olsonii,* the *Phoma* genus fungus is *Phoma multirostrata*, and the *Trichoderma* genus fungus is *Trichoderma asperellum.*

* * * * *